United States Patent
Knox et al.

(10) Patent No.: US 9,271,684 B2
(45) Date of Patent: Mar. 1, 2016

(54) CT IMAGING APPARATUS AND METHODS

(71) Applicant: Elekta AB (publ), Stockholm (SE)

(72) Inventors: Christopher Knox, East Grinstead (GB); Colin Winfield, Crawley (GB); Kevin Brown, Horsham (GB)

(73) Assignee: Elekta AB (Publ), Stockholm (SE)

( * ) Notice: Subject to any disclaimer, the term of this patent is extended or adjusted under 35 U.S.C. 154(b) by 246 days.

(21) Appl. No.: 13/956,605

(22) Filed: Aug. 1, 2013

(65) Prior Publication Data

US 2013/0315367 A1     Nov. 28, 2013

Related U.S. Application Data

(63) Continuation of application No. PCT/EP2011/000511, filed on Feb. 4, 2011.

(51) Int. Cl.
| | |
|---|---|
| *A61B 6/03* | (2006.01) |
| *A61B 6/00* | (2006.01) |
| *A61N 5/10* | (2006.01) |

(52) U.S. Cl.
CPC ............... *A61B 6/032* (2013.01); *A61B 6/4233* (2013.01); *A61B 6/466* (2013.01); *A61N 2005/1061* (2013.01)

(58) Field of Classification Search
CPC ........ A61B 6/032; A61B 6/06; A61B 6/4035; A61B 6/4085
See application file for complete search history.

(56) References Cited

U.S. PATENT DOCUMENTS

| | | | |
|---|---|---|---|
| 2004/0013239 A1 | 1/2004 | Gregerson | 378/197 |
| 2005/0265515 A1 | 12/2005 | Tashiro | 378/20 |
| 2007/0237290 A1 | 10/2007 | Mostafavi | 378/21 |
| 2008/0317196 A1* | 12/2008 | Imai et al. | 378/8 |
| 2011/0080990 A1* | 4/2011 | Filiberti et al. | 378/4 |

OTHER PUBLICATIONS

Cho, et al., *Region-of-Interest Image Reconstruction with Intensity Weighting in Circular Cone-Beam CT for Image-Guided Radiation Therapy*, Medical Physics, AIP vol. 36, No. 4, Mar. 13, 2009, pp. 1184-1192.
International Search Report dated Sep. 23, 2011, 3 pages.

* cited by examiner

*Primary Examiner* — Hoon Song
(74) *Attorney, Agent, or Firm* — Sunstein Kann Murphy & Timbers LLP

(57) ABSTRACT

An apparatus has a patient support, a rotatable gantry supporting a source of imaging radiation, and a radiation detector that operates in a cyclical pattern of an exposure phase followed by a readout phase. For a first detector cycle in which the gantry has a first angle of rotation, the source of radiation is controlled to emit a first radiation beam pulse during the exposure phase, and respective first imaging data is read out during the readout phase. For a second, subsequent detector cycle, it is determined if the gantry has rotated through at least a threshold angular displacement relative to said first angle of rotation, and if so, the source of radiation is controlled to emit a second radiation beam pulse during the exposure phase, and respective second imaging data is read out during the readout phase.

10 Claims, 3 Drawing Sheets

CT IMAGING APPARATUS AND METHODS

This application is a continuation of co-pending Patent Cooperation Treaty Patent Application PCT/EP2011/000511, filed Feb. 4, 2011 and published as WO 2012103901 A1 on Aug. 9, 2012, which is incorporated herein by reference.

TECHNICAL FIELD

The present invention relates to methods and apparatus for computed tomography (CT) scanning. Various embodiments are described, including methods suitable for surveillance of a patient during radiotherapy treatment.

BACKGROUND ART

It is known that exposure of human or animal tissue to ionizing radiation will kill the cells thus exposed. This finds application in the treatment of pathological cells, for example. In order to treat tumors deep within the body of the patient, the radiation must first penetrate the healthy tissue in order to irradiate and destroy the pathological cells. In conventional radiation therapy, large volumes of healthy tissue can thus be exposed to harmful doses of radiation, resulting in prolonged recovery periods for the patient. It is therefore desirable to design a device for treating a patient with ionizing radiation and treatment protocols so as to expose the pathological tissue to a dose of radiation which will result in the death of those cells, whilst keeping the exposure of healthy tissue to a minimum.

Several methods have previously been employed to achieve the desired pathological cell-destroying exposure whilst keeping the exposure of healthy cells to a minimum. Many methods work by directing radiation at a tumor from a number of directions, either simultaneously from multiple sources or multiple exposures from a single source. The intensity of radiation emanating from each direction is therefore less than would be required to actually destroy cells (although still sufficient to damage the cells), but where the radiation beams from the multiple directions converge, the intensity of radiation is sufficient to deliver a therapeutic dose. By providing radiation from multiple directions, the amount of radiation delivered to surrounding healthy cells can be minimized. Of course it is also important that the radiation should be accurately targeted on the region that requires treatment. For this reason, patients are required to remain still for the duration of the therapy session, to minimize the risk of damage to healthy tissue surrounding the target region. However, some movement is inevitable, e.g. through breathing, or other involuntary movements. To overcome this problem, it is known to integrate an image acquisition system with the radiotherapy apparatus, to provide real-time imaging of the region (i.e. surveillance) and ensure that the radiation emitted by the radiotherapy apparatus is not misdirected.

One such integrated image acquisition system is a computed tomography (CT) scanner. In these systems, a source of kV radiation emits a cone beam of radiation towards the patient, with the scattered radiation being detected by an imager positioned substantially opposite the source. The projection images, acquired at a range of angles around the patient, can then be reconstructed using known techniques to provide a three-dimensional image of the region undergoing therapy. In addition, single projection images can be used to detect the instantaneous position of the patient anatomy during radiotherapy.

Currently the kV projection images required for a 3D volume/CBCT scan are acquired at a constant rate as the gantry rotates around the isocenter during treatment. For example, kV projection images required for surveillance, i.e. ensuring the patient has not moved during treatment, may be acquired at the readout rate of the detector.

SUMMARY

The limitation of acquiring projection images at a constant rate is that if the gantry slows or stops during a 3D volume/CBCT scan, the number of projection images that are acquired will exceed the number needed to achieve the required image quality. This means that the patient will have received unnecessary kV exposures, leading to an excessive and inconsistent dose delivered to the patient.

Embodiments of the present invention seek to overcome these and other problems by providing an image acquisition methodology that serves to reduce the amount of dose delivered to the patient while maintaining an acceptable image quality and effectively monitoring the position of the patient.

In a first aspect of the present invention, there is provided a method of imaging a patient, in an apparatus comprising a patient support on which the patient may be positioned, and a rotatable gantry supporting a source of imaging radiation for generating a radiation beam towards the patient, and a detector for detecting the radiation beam after interaction with the patient, the detector operating in a cyclical pattern of an exposure phase followed by a readout phase. The method comprises, for a first detector cycle in which the gantry has a first angle of rotation, controlling the source of radiation to emit a first radiation beam pulse during the exposure phase, and reading out respective first imaging data during the readout phase. The method further comprises, for a second, subsequent detector cycle, determining if the gantry has rotated through at least a threshold angular displacement relative to said first angle of rotation, if so, controlling the source of radiation to emit a second radiation beam pulse during the exposure phase, and reading out respective second imaging data during the readout phase.

So, embodiments of the present invention provide an imaging method in which further images are acquired once the gantry has rotated through a certain angular displacement (e.g. five degrees) since the last image was acquired. The method is not concerned with the absolute angle of the gantry (i.e. the angle relative to the stationary parts of the apparatus), merely with the relative angle since the last image was acquired. This concept will be discussed in further detail below.

In embodiments of the invention, the beam of radiation may be emitted even if the threshold angular displacement has not been reached. For example, if the rotation of the gantry slows significantly (or even reverses direction), the amount of time between acquisition of successive images may be too long to properly monitor the current position of the patient. In these embodiments, the method further comprises, for the second detector cycle, determining if a threshold period of time has elapsed since the first radiation beam pulse and, if so, controlling the source of radiation to emit said second radiation beam pulse during the exposure phase.

Embodiments of the present invention are useful both for surveillance (where individual images are used to monitor the position of the patient), and more conventional CT imaging (where two-dimensional images are combined to reconstruct a three-dimensional image). Thus, in an embodiment of the present invention, the apparatus further comprises a source of therapeutic radiation, and the source of therapeutic radiation and the rotatable gantry are controlled according to a treatment plan specifying a variable rate of rotation.

In embodiments of the present invention, the projection images acquired may be used on their own, to determine the position of the patient in a two-dimensional image, or combined into a dataset and used to reconstruct a volume image of the patient.

The second detector cycle may follow successively after the first cycle, or later than that. For example, in embodiments of the present invention the apparatus may check the angular displacement of the gantry only on integer multiples of the detector cycle, e.g. every second or every third cycle.

DETAILED DESCRIPTION

Figure 1:
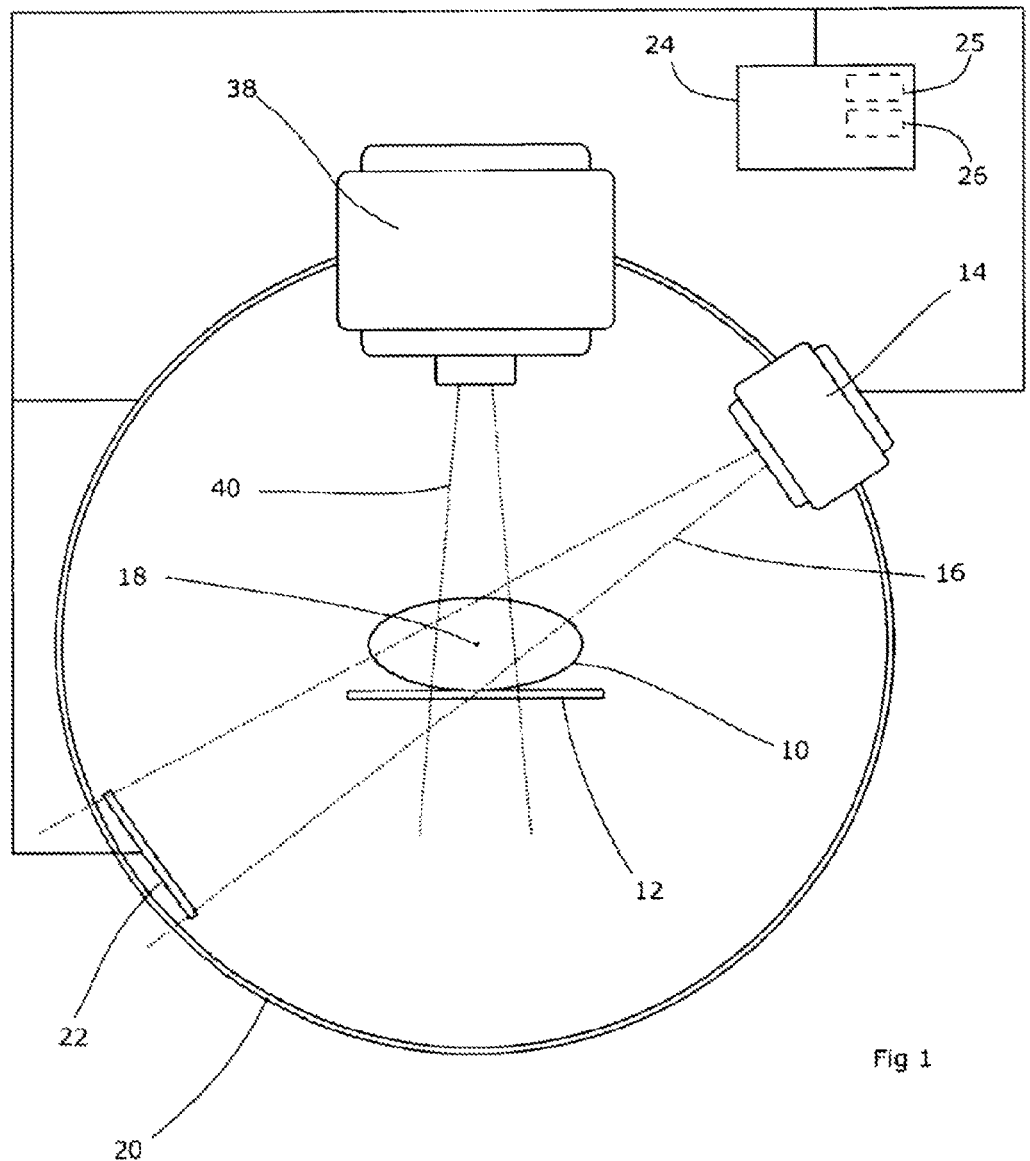
FIG. 1 shows an apparatus according to embodiments of the present invention.

FIG. 1 is a schematic diagram showing an apparatus according to embodiments of the present invention.

A patient 10 is supported on a couch 12 which may be of any suitable design. Couches typically allow the elevation, latitudinal and longitudinal position of the patient to be adjusted, and this may be provided for as desired. The couch 12 may also allow rotation in up to three rotational degrees of freedom (pitch, yaw and roll).

An x-ray source 14 is arranged to project a wide beam 16 of radiation generally directed towards the isocenter 18 of the system. The source 14 is rotatable around the isocenter 18 on a rotational support 20. The support can, for example, be in the form of a ring or annulus around the patient 10 and couch 12 in which the source is mounted, or it can be a C-arm, or any suitable support allowing the source to rotate, or any combination thereof. The radiation beam 16 will generally have an energy in the kV range, as that is most suitable for imaging purposes.

A two-dimensional flat-panel detector 22 is also mounted on the support 20, opposite the source 14 and arranged to rotate in synchronism therewith. If the support includes a C-arm then this can be achieved by mounting the detector on the opposite arm. Thus, radiation emitted by the source 14 is partially absorbed by the patient and the attenuated, scattered signal is detected by the flat panel detector 22.

The apparatus further comprises cables linking the source 14, detector 22 and rotational support 20 to processing means 24, which controls their respective operation, and processes the data generated including the images, source intensity (etc.), and rotational support position (including, for example, the rotational angle, translational position, etc.). In addition to performing these functions, the processing means 24 comprises timing circuitry 25 and positioning circuitry 26, which will be explained in greater detail below. Data is output via any suitable means, e.g. a monitor but not limited thereto, and the system is controlled by any suitable input means, e.g. a keyboard but likewise not especially limited thereto.

In the illustrated embodiment, the apparatus further comprises a source of therapeutic radiation 38 arranged to emit a suitably collimated beam of therapeutic radiation 40. Thus, imaging can take place during treatment. However, in other embodiments the apparatus may be a "pure" imaging apparatus, without the source of therapeutic radiation.

Figure 2:
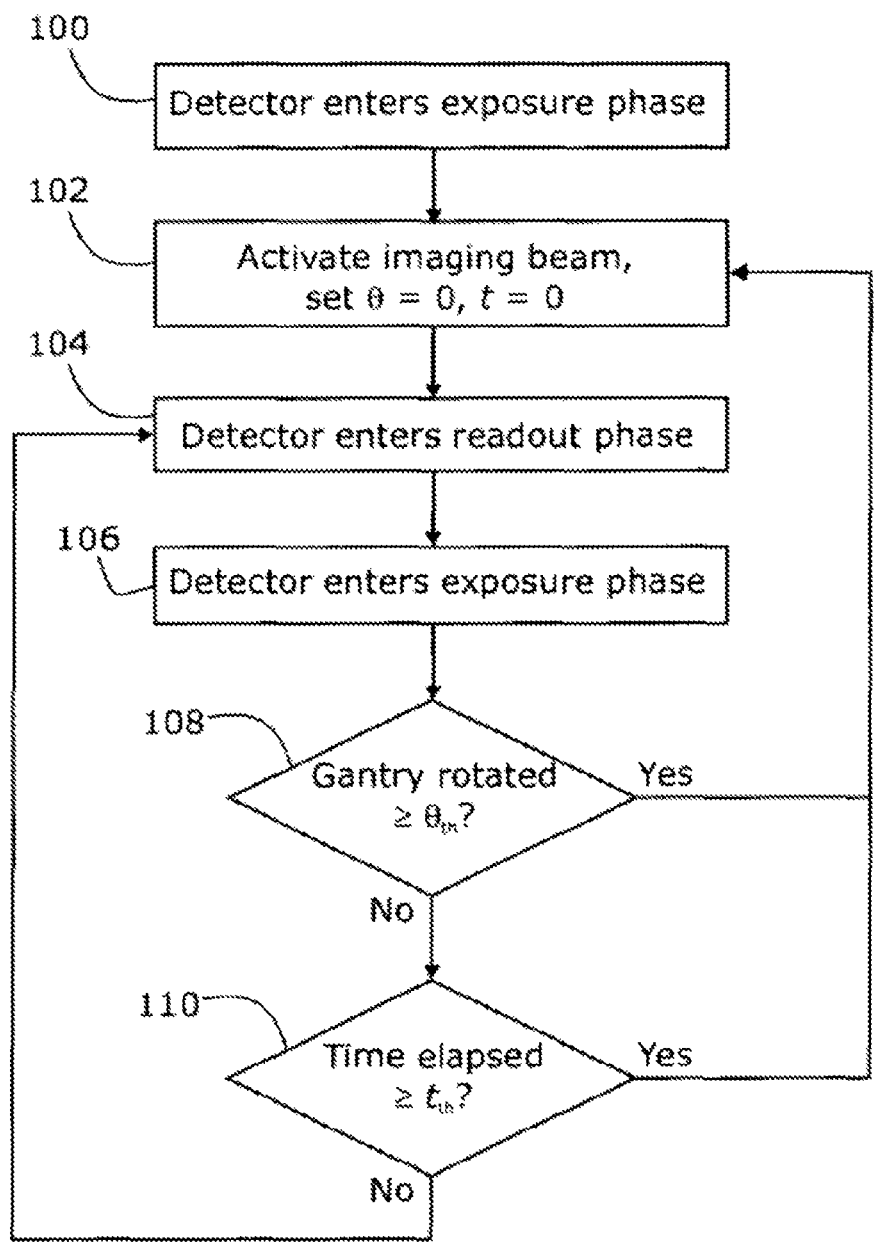
FIG. 2 is a flow chart of a method according to embodiments of the present invention.
Figure 3A:
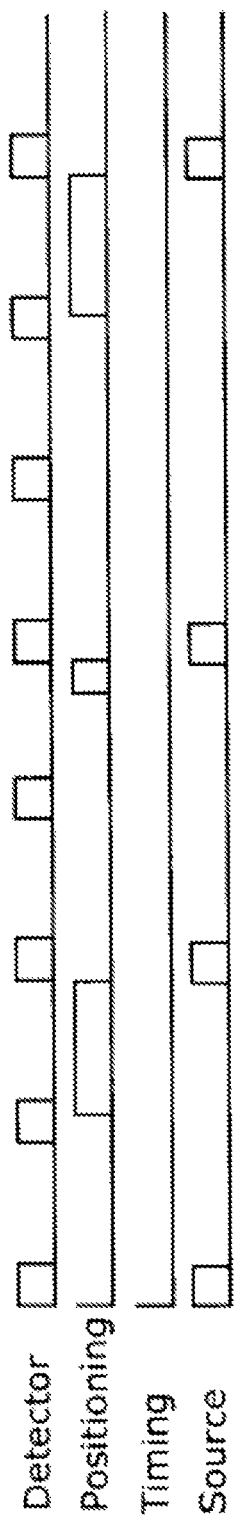
FIGS. 3A and 3B are signaling diagrams showing the timing of signals according to embodiments of the present invention.
Figure 3B:
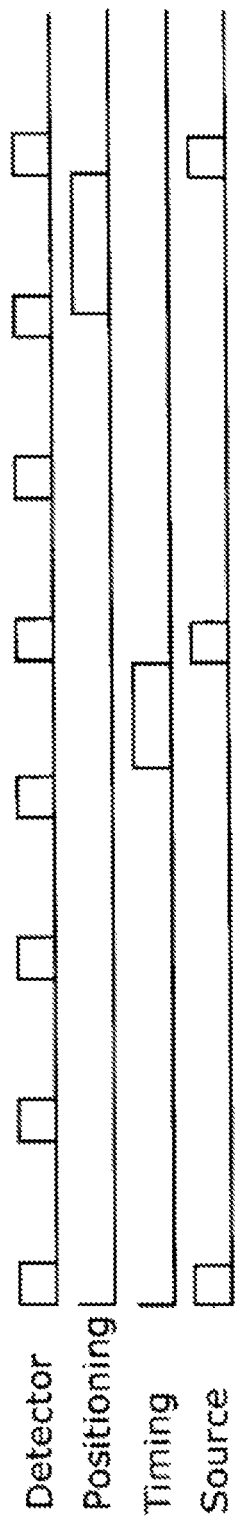

FIG. 2 is a flow chart of a method according to embodiments of the present invention. FIGS. 3a and 3b show examples of signaling diagrams for the detector 22, the positioning circuitry 26, the timing circuitry 25, and the source 14.

It has been mentioned above that the detector 22 is operated in a continuous cycle of exposure followed by readout. This is shown most clearly in FIGS. 3a and 3b, where the uppermost line represents the state of the detector 22. A "high" signal in the Figures represents the exposure phase; the detector receives any incoming radiation, with the accumulated charge stored in an array of pixels. A "low" signal in the Figures represents the readout phase; the pixels are no longer open to incoming radiation, and scanning electronics enables the accumulated charge in each pixel to be read out and passed to the processing means 24. In this way, the charge stored in the pixels of the detector 22 is continually reset to zero (or some other null value). So-called dark currents and other noise do not have time to build up in the pixels, and image quality is kept high.

The method begins in step 100, when the detector enters an exposure phase. For this (arbitrarily chosen) exposure phase, the radiation source 14 is controlled to emit a pulse of radiation (step 102). The pulse is timed to coincide with the exposure phase so that the radiation scattered from the patient can be detected. Also as part of step 102, θ is set to zero in the positioning circuitry 26, and t is set to zero in the timing circuitry 25. θ represents the rotation of the gantry 20 relative to its angle at the time of the previous pulse emitted by the source 14. In this context, θ is an angular displacement, i.e. it can be positive or negative depending on the direction of rotation, t represents the time elapsed since the previous pulse was emitted by the source 14.

In step 104, the detector 22 enters the subsequent readout phase. Scanning electronics in the detector reads out the charge accumulated during the previous exposure phase, and passes the data to processing means 24.

In due course (step 106), the detector 22 enters the next exposure phase as part of its continuous cycle. At this point, the processing means 24 has to make a decision as to whether to emit a further pulse of radiation with the source 14. In step 108, positioning circuitry 26 compares the current relative rotation θ to a threshold value, $\theta_{th}$. If the gantry 20 has rotated at least that far since the previous pulse of radiation (in step 102), the source 14 of radiation is activated and the method moves back to step 102. θ and f are reset as before. Note that θ and $\theta_{th}$ are vector quantities having a direction as well as a magnitude. If $\theta_{th}$ is equal to +5° (for example) and the instantaneous value of θ is −6°, θ is not considered greater than $\theta_{th}$. Note that none of this is intended to convey a preferred direction of rotation. The gantry 20 may rotate mainly in a clockwise direction or mainly in an anticlockwise direction, with the threshold angular displacement $\theta_{th}$ being set accordingly in either case.

If the gantry has not rotated that far, the method proceeds to step 110, where the timing circuitry 25 compares the current elapsed time t with a threshold value $t_{th}$. If sufficient time has elapsed since the last radiation pulse (i.e. is t is equal to or greater than $t_{th}$), the source 14 of radiation is activated and the method moves back to step 102. θ and t are reset as before.

If t is less than $t_{th}$, the method proceeds to step 104. That is, no action is taken by the processing means 24 and the detector simply moves forward to its next readout phase. For this phase, no significant data will be acquired; the data readout from the detector 22 will either be null or can be discarded.

Those skilled in the art will realize that the method presented in FIG. 2 may be subject to alterations without departing from the scope of the invention as defined in the claims appended hereto. The order of steps may be altered significantly in practice. For example, for clarity the flow chart shows the processing means 24 checking θ and t only after the detector has entered an exposure phase. In practice, it may well be necessary to perform steps 108 and 110 before the detector enters such an exposure phase to allow time to control the source of radiation appropriately. Further, steps 108 and 110 may be performed in the reverse order without affecting the operation of the apparatus.

The processing means 24 may not check θ and t to coincide with every exposure phase. While this represents something of an ideal, in that under that regime a pulse of radiation will be emitted as soon as possible after the required rotational or timing thresholds have been met, it may not be practical to process that information constantly. To reduce the computational complexity, θ and t may be checked only once every integer multiple of exposure phases (e.g. every second, third or fifth exposure phase etc.).

It will be clear from the above that the absolute angle of image acquisition is unimportant for the purposes of the present invention, as the detector is operated in a continuous loop of exposure followed by readout and the radiation pulses are timed to coincide the an exposure phase. The repeated detector cycle has the benefit of minimizing buildup of dark current or other noise, but at the cost of reduced certainty in the absolute angle of the gantry. That is, the apparatus emits a beam of radiation timed to coincide with an exposure phase after the gantry has rotated through the threshold angular displacement. Therefore, the angular displacement at the time of the image acquisition will in general be equal to the threshold plus some further movement.

FIG. 3a shows an example of signaling where the gantry is rotated at a varied, but reasonable and consistent speed. The detector 22 cycles through exposure followed by readout. At various points, the positioning circuitry 26 detects that the gantry has rotated by more than $t_{th}$. At these points the positioning circuitry signal goes high, and at the next available exposure phase the source is activated. The speed of rotation in this example is such that at no point is $£_h$ reached. The apparatus emits pulses of radiation based solely on the rotation of the gantry.

FIG. 3b shows an example where the rotation of the gantry is more erratic. After the first, initial pulse of radiation, the gantry 20 takes too long to rotate through $6_{th}$—For example, it have rotated too slowly, have stopped completely, or even reversed direction. In this example, $t_{th}$ is reached before the gantry rotates through $θ_{th}$. Thus, the signal of the timing circuitry 25 goes high, and at the next available exposure phase the source is controlled to emit a pulse of radiation. Subsequently, the rotation of the gantry speeds up as $θ_{th}$ (relative to the second pulse of radiation) is reached before $t_{th}$.

Embodiments of the present invention thus provide methods and apparatus for imaging a patient without exposing him or her to unnecessary radiation doses. In addition, embodiments of the present invention include a failsafe should an unacceptable period of time have elapsed since the last image acquisition, allowing the method to be used in surveillance of the patient during therapy, for example.

It will of course be understood that many variations may be made to the above-described embodiment without departing from the scope of the present invention.

What is claimed is:

1. A method of imaging a patient in an apparatus comprising:
   a patient support on which the patient may be positioned, and a rotatable gantry supporting:
   a source of imaging radiation for generating a radiation beam towards the patient, and
   a detector for detecting the radiation beam after interaction with the patient, the detector operating in a cyclical pattern of an exposure phase followed by a readout phase,
   the method comprising:
   for a first detector cycle, in which the gantry has a first angle of rotation,
   controlling the source of imaging radiation to emit a first radiation beam pulse during the exposure phase, and
   reading out respective first imaging data during the readout phase;
   for a second, subsequent detector cycle,
   determining if the gantry has rotated through at least a threshold angular displacement relative to said first angle of rotation,
   if so, controlling the source of imaging radiation to emit a second radiation beam pulse during the exposure phase, and reading out respective second imaging data during the readout phase.

2. The method according to claim 1, wherein the first radiation beam pulse is emitted at a first point in time, and the method further comprises:
   for said second detector cycle, determining if a threshold period of time has elapsed since said first point in time and, if so, controlling the source of imaging radiation to emit said second radiation beam pulse during the exposure phase.

3. The method according to claim 1, wherein the rotatable gantry further supports a source of therapeutic radiation, and the source of therapeutic radiation and the rotatable gantry are controlled according to a treatment plan which is delivered at a varying rate of rotation.

4. The method according to claim 1, wherein said second detector cycle follows said first detector cycle successively.

5. The method according to claim 1, further comprising:
   reconstructing a volume image of said patient using a dataset comprising at least the imaging data from said first and second detector cycles.

6. An apparatus for imaging a patient, comprising:
   a patient support configured to position the patient;
   a rotatable gantry supporting a source of imaging radiation configured to generate a radiation beam towards the patient; and
   a detector configured to detect the radiation beam after interaction with the patient, the detector operating in a cyclical pattern of an exposure phase followed by a readout phase; and
   control and imaging circuitry configured to:
   for a first detector cycle, in which the gantry has a first angle of rotation:
   control the source of imaging radiation to emit a first radiation beam pulse during the exposure phase, and
   read out respective first imaging data during the readout phase;
   for a second, subsequent detector cycle:
   determine if the gantry has rotated through at least a threshold angular displacement relative to said first angle of rotation, and if so, control the source of imaging radiation to emit a second radiation beam pulse during the exposure phase, and read out respective second imaging data during the readout phase.

7. The apparatus according to claim 6, wherein the first radiation beam pulse is emitted at a first point in time, and the control and imaging circuitry is further configured to:
for said second detector cycle, determine if a threshold period of time has elapsed since said first point in time and, if so, control the source of imaging radiation to emit said second radiation beam pulse during the exposure phase.

8. The apparatus according to claim 6, wherein the rotatable gantry further supports a source of therapeutic radiation, and the source of the therapeutic radiation and the rotatable gantry are controlled according to a treatment plan which is delivered at a varying rate of rotation.

9. The apparatus according to claim 6, wherein said second detector cycle follows said first detector cycle successively.

10. The apparatus according to claim 6, wherein the control and imaging circuitry is further arranged to reconstruct a volume image of said patient using a dataset comprising at least the imaging data from said first and second detector cycles.

\* \* \* \* \*